United States Patent [19]

Kers et al.

[11] Patent Number: 5,531,707
[45] Date of Patent: Jul. 2, 1996

[54] DEVICE FOR INTRODUCING A SUBSTANCE INTO A BODY CAVITY OF A PATIENT

[75] Inventors: Tore A. Kers, Södertälje; Kenneth B. Andersson, Kristinehamn, both of Sweden

[73] Assignee: Ab Astra, Sodertalje, Sweden

[21] Appl. No.: 956,758

[22] PCT Filed: Jun. 4, 1991

[86] PCT No.: PCT/SE91/00391

§ 371 Date: Jan. 15, 1992

§ 102(e) Date: Jan. 9, 1992

[87] PCT Pub. No.: WO91/18640

PCT Pub. Date: Dec. 12, 1991

[30] Foreign Application Priority Data

Jun. 8, 1990 [SE] Sweden ............................ 9002065
Mar. 27, 1991 [AU] Australia .......................... 73833/91

[51] Int. Cl.⁶ .............................. A61M 5/24; A61M 5/28
[52] U.S. Cl. .................... 604/200; 604/68; 604/192; 604/199; 604/239; 604/263; 604/279; 222/591.6; 425/441; 425/443; 249/63
[58] Field of Search ................... 604/68, 117, 129, 604/148, 192, 197, 199, 200, 215, 236, 238, 239, 240, 244, 256, 263, 268, 271, 274, 275, 278, 279, 187, 264; 222/541, 107, 212, 215, 541.1, 541.3, 541.4, 541.6, 541.7, 541.9; 425/441, 443, DIG. 5, 442; 264/318; 249/161, 162, 63

[56] References Cited

U.S. PATENT DOCUMENTS

| | | |
|---|---|---|
| 2,859,478 | 11/1958 | Glasson . |
| 3,289,252 | 12/1966 | Bromley . |
| 3,366,289 | 1/1968 | Badavas et al. . |
| 3,373,460 | 3/1968 | Ladney, Jr. . |
| 3,416,712 | 12/1968 | Shastal ................................ 222/541 |
| 4,052,986 | 10/1977 | Scaife ................................. 222/541 |
| 4,112,942 | 9/1978 | Scaife . |
| 4,209,160 | 6/1980 | Vanotti . |
| 4,319,701 | 3/1982 | Cambio ............................... 222/541 |
| 4,619,645 | 10/1986 | Hussey ................................ 604/200 |
| 4,765,518 | 8/1988 | O'Meara ............................. 222/541 |
| 4,850,970 | 7/1989 | Sutherland .......................... 604/192 |
| 4,926,915 | 5/1990 | Deussen et al. .................... 604/200 |
| 4,981,472 | 1/1991 | Ennis, III et al. .................. 604/239 |
| 5,053,020 | 10/1991 | Manchester ........................ 604/275 |

FOREIGN PATENT DOCUMENTS

| | | |
|---|---|---|
| 386123 | 3/1978 | Austria . |
| 1766917 | 9/1971 | Germany . |
| 118988 | 3/1970 | Norway . |
| 608373 | 1/1979 | Switzerland . |

Primary Examiner—C. Fred Rosenbaum
Assistant Examiner—Ronald Stright, Jr.
Attorney, Agent, or Firm—White & Case

[57] ABSTRACT

The invention relates to disposable devices for introducing substances into body cavities of a patient. The device comprises a container for holding a substance which is connected to a tube ending in an opening which is inserted into a body cavity. The opening is sealed by a frangible seal located inside the opening. An actuating rod ruptures and removes the seal upon actuation. The actuating rod is provided with supporting rods extending to the container which are connected to the container by frangible connections. The supporting rod serves as a safe-guard against accidental rupture of the seal and as a guide for a controlled movement of said the actuating rod. The supporting rod also defines and protects an area to be kept sterile. The invention also relates to a moulding apparatus and to a method for making said device.

16 Claims, 10 Drawing Sheets

DEVICE FOR INTRODUCING A SUBSTANCE INTO A BODY CAVITY OF A PATIENT

TECHNICAL FIELD OF THE INVENTION

The present invention relates to a prefilled, disposable device for introducing a pharmacologically active substance, preferably in the form of a jelly, into a body cavity of a patient, for instance into the urethra, comprising a container for the substance and a tubular part communicating with the container and intended to be inserted into said cavity, said tubular part ending in an opening having a frangible seal with an inner side facing the inside of said device and an outer side facing the outside, said seal being located a slight distance within said opening and preferably being in the form of a membrane, the outer side of said seal further being provided with an integrally formed actuating rod projecting through said opening to the outside of the device, said actuating rod being arranged to rupture and remove said seal upon actuation and before the insertion of said tubular part into said body cavity, the parts of the walls of the tubular part being located on the outer side of said seal further being provided with rounded edges in order to alleviate any discomfort which may be experienced by the patient when the tubular part is inserted into said body cavity.

The invention also relates to method and a mould apparatus for manufacturing the invention.

BACKGROUND OF THE INVENTION

It is sometimes necessary to introduce pharmacologically active substances into body cavities, such as the urethra or the rectum of a patient. One instance of this is the introduction of a local anesthetic into the urethra prior to the insertion of a catheter or similar into the urethra in order to alleviate the discomfort and pain experienced by the patient during this operation. The local anesthetic may for instance be introduced through a tubular part inserted into the body cavity in question.

In order that the patient may not experience the same discomfort during the introduction of the anesthetic as during the actual insertion of the catheter, very high demands have to be made on the shape and smoothness of the tubular part and particularly on the tip thereof.

These demands easily can be met if a reusable, tubular part made of a permanent material without an integral seal is used in accordance with the long-established prior art. However, such a tubular part normally would have to be sterilized before a renewed use which is one reason why they no longer are much in use.

Instead prefilled, disposable devices are nowadays used extensively in hospitals, medical practices etc. These devices are normally delivered in a sterile condition in the form of sealed containers normally having a frangible seal in or on a dispensing outlet. In a device of the kind mentioned above in the introduction, the dispensing outlet of course would be the opening in the tubular part. When designing the frangible seal, the fact that this opening may not have any sharp edges after removal of the frangible seal must be taken into consideration, since such sharp edges would cause the patient pain or other discomfort when the tubular part is inserted into the body cavity.

One solution to this problem is disclosed in AT-B-386 123. This document discloses a device for introducing a lubricating substance into the urethra in order to facilitate a subsequent insertion of a catheter. The device comprises two parts, namely a bellow-shaped container and a funnel-shaped part ending in a tubular part. The free end of the tubular part is sealed by means of a frangible seal. The container and the funnel-shaped part are ultrasonically welded together. The opening at the free end of the tubular part has rounded edges and the frangible seal is located a slight distance within the tubular part. The frangible seal is provided with an integrally formed actuating rod projecting outside the opening and the frangible seal is broken upon actuation of the rod.

CH-A-608 373 discloses another device of the same general kind as the prior art device described above, the main difference being the field of application, which in this case is the introduction of a pharmacologically active substance into the rectum of a patient.

There are however some factors that have to be considered when designing and manufacturing a device of the kind described above. When such a device is opened, the frangible seal always should be ruptured in a clearly defined way without leaving any projecting parts or loose splinters which may inconvenience or harm the patient. This means that a very high standard must be met in regard of the homogenity of the material in the actuating rod, in the frangible seal and in the tubular part as well as in regard of the accuracy in size of these parts.

The frangible seal also should be ruptured in said clearly defined way irrespective of the manner in which the actuating rod is operated.

Depending on the kind of body cavity into which the tubular part is to be inserted, a high standard may have to be set regarding the sterility of the tubular part, particularly if the cavity in question is the urethra.

BRIEF DESCRIPTION OF THE INVENTIVE CONCEPT

The present invention aims to provide a device of the kind described above which meets these high standards. This is achieved in that said actuating rod at its outer end is provided with at least one supporting rod which is formed integrally with said actuating rod and which extends to said container, said supporting rod being connected to said container by means of a frangible connection, by which means said supporting rod serves as a safe-guard against an accidental rupturing of said seal and as a guide for a controlled movement of said actuating rod, when actuated, in order to ensure a correct rupture of said frangible seal as well as to serve as a handle for actuating said actuating rod, said supporting rod in conjunction with said actuating rod also defining and protecting an area of said tubular part which is to be kept sterile.

The above-mentioned object of the invention further is achieved by means of a method of manufacturing said device from a thermoplastic material by injection-moulding said device in a mould apparatus comprising a core having the general configuration of the inner side of said container and said tubular part, said core being located in a mould having the general configuration of the outer side of said device, including said actuating rod and said supporting rod, the thermoplastic material being injected in molten form into said mould at that part of said mould which defines said supporting rod and/or said actuating rod, by which means said molten material is forced to pass mainly through the annular space in said mould defining said frangible seal before forming the container and said tubular part.

The object of the invention further is achieved in that said device is made in a mould apparatus comprising a mould containing a core, said mould defining the outer side of said device and said core defining the inner side of said container and said tubular member, said core and said mould being longitudinally movable with respect to each other for opening said mould and for the ejection of said device, said core further being longitudinally movable with respect to said mould by means of a micrometer adjustment screw, by which means the thickness of said seal defined between the tip of said core and said mould at the end of said tubular part can be finely adjusted before and during the manufacturing process.

SHORT DESCRIPTION OF THE APPENDED DRAWINGS

A preferred embodiment of the invention is shown in the appended drawings which should be studied in conjunction with detailed description given below. It should be noted that expressions such as "upper", "lower", "downwards", "horizontal", "vertical" etc contained in this description only are used as expressions of convenience relating to the specific vertical orientation of the mould apparatus for manufacturing the device as illustrated in the drawings and should not be construed as limiting terms.

For the sake of clarity, the reference signs are not repeated throughout all the drawings.

FIG. 1 is a longitudinal view of the device,

FIG. 2 is a view showing the device rotated 90 degrees relative to the view in FIG. 1, FIG. 3 is an enlarged part view, partly broken away, of the end of the tubular part showing the frangible seal and the actuating rod (detail B in FIG. 1), FIG. 3a is an enlarged view of detail C in FIG. 3, FIG. 3b is an enlarged view of detail A in FIG. 1, FIG. 3c shows section I—I in FIG. 3b, FIG. 4 is a vertical half-section through a mould apparatus having a mould for manufacturing a device according to the invention, in a closed state, FIG. 5 is a vertical section of the apparatus taken along the line V—V in FIG. 4, FIG. 6 is a vertical section corresponding to FIG. 4 but in which the mould apparatus is beginning to open, FIG. 7 is an enlarged detail A of FIG. 6 showing those parts of the mould which shape the tube and the actuating rod in vicinity of the frangible seal in the first step of releasing the finished product, corresponding to the situation in FIG. 7, FIG. 8 is a vertical section corresponding to the one shown in FIG. 6, but illustrating the next step in opening the mould, FIG. 9 is an enlarged detail B of FIG. 8 showing the lower end of the adjustment rod, FIG. 10 is a vertical section corresponding to the one shown in FIG. 8, but illustrating a further step in opening the mould, FIG. 11 is a vertical section corresponding to the one shown in FIG. 10, but illustrating the final step in opening the mould and the ejection of the finished product, and FIG. 12 is a vertical section taken along the line XII—XII in FIG. 11.

DETAILED DESCRIPTION OF A PREFERRED EMBODIMENT OF THE INVENTION

Figure 1:
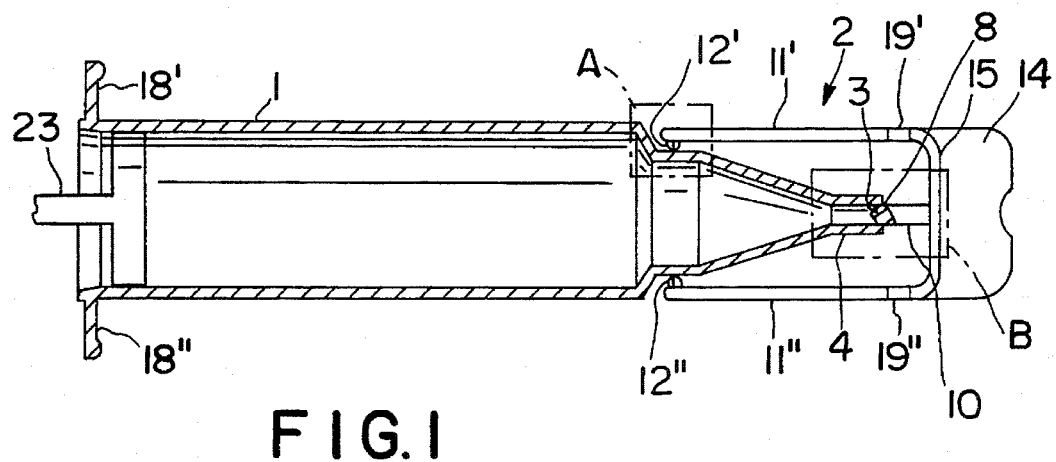
Figure 2:
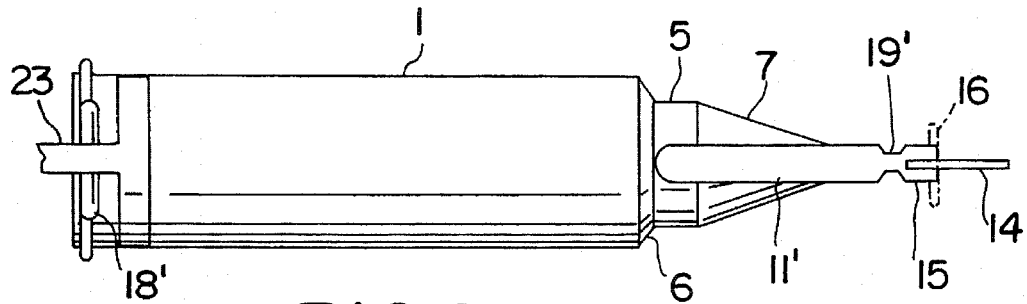

As can be seen in FIGS. 1–3c, the device in its preferred embodiment has the general shape of a syringe with a cylindrical container 1. The cylinder 1 is open at one end and closed at the other end by means of an integrally formed tubular part 2 having a frangible seal 3. The open end of the cylinder 1 may be closed by means of a plunger (not shown) and the contents of the cylinder 1 may be ejected through the tubular part 2 by means of the plunger when the seal 3 has been ruptured, for which purpose the cylinder is provided with two holding tabs 18',18" adjacent the open end, as normal in syringes.

The end of the cylinder carrying the tubular part 2 has an inwardly directed flange or shoulder 6 which may be obliquely oriented relative to the longitudinal axis of the cylinder so that it forms a truncated cone with the narrow end facing away from the cylinder, said narrow end defining a circular opening which is concentric with the longitudinal axis of the cylinder. The tubular part 2 comprises a relatively short cylindrical part 5 which is connected to the shoulder 6 at said opening defined by said shoulder 6 and which merges into a conically tapering part 7 ending into a tube 4. The free end of this tube 4 ends in an opening 8 having an edge 9 with a smoothly rounded contour. In this particular case, a section through the edge 9 would have a shape being about half-circularly curved, FIG. 3, the ends of the half-circle merging continuously into the inner side and in the outer side of the tube 4 respectively. The frangible seal 3 is located at the juncture of the curved part or edge 9 to the inner side of the tube 4 or slightly within this juncture and is in the form of a comparatively thin membrane. An actuating rod 10 formed integrally with the membrane extends coaxially with the tube 4 from the center of the membrane past the edge 9. The side of the membrane not carrying the actuating rod may be provided with a half-spherical part 17 being concentric with the actuating rod. The primary function of this half-spherical part 17 is to collect air bubbles entrained with the thermoplastic material when the device is injection-moulded in order to prevent that such air bubbles remain in the membrane, which might render this inoperative, or in the actuating rod close to the membrane, which might cause the rod to break rather than the membrane.

Figure 3:
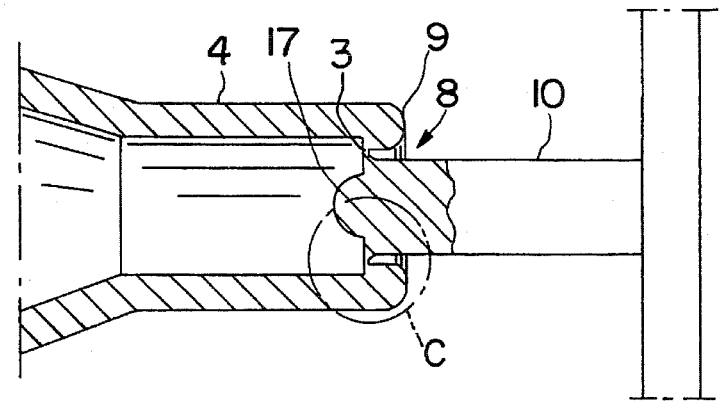
Figure 3A:
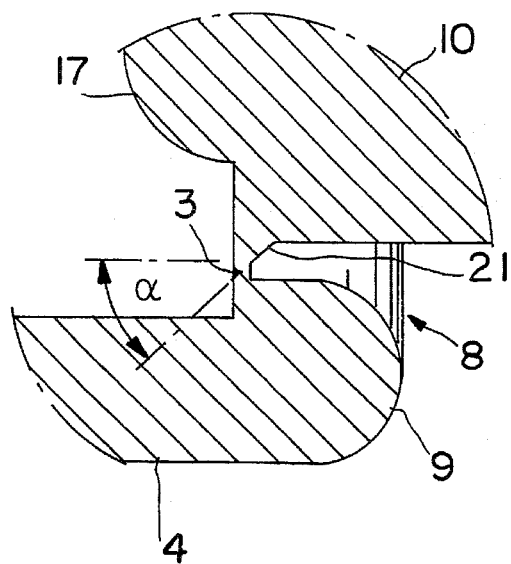

Although the thickness of the actuating rod, as illustrated in FIG. 3, has been chosen to be smaller than the inner diameter of the tube, resulting in that the membrane 3 has a pronounced extent, the actuating rod of course may be widened conically or otherwise at the juncture to the membrane. FIG. 3a illustrates how the rod 10 ends in a conical part 21 joined to the membrane 3. A suitable base angle $\alpha$ of the conical part 21 may be 42 degrees.

This widening of the rod may even be done such that the widened part of the actuating rod actually is in direct contact with the inner side of the tube 4 along a band-shaped part of its periphery, the width of said band-shaped part essentially corresponding to the thickness of the membrane. This widened part may have a half-spherical shape being complementary to the half-spherical part 17, thus in principle forming a ball-joint in the end of the tube 4 which is attached to the inner side of the tube in a band-shaped, peripheral area, the actuating rod extending out from the ball-joint through the opening at the end of the tube. From the view-point of manufacturing the device by means of the mould apparatus described below it is however preferable that the membrane has a width which is about the same as the thickness of the membrane irrespective of whether the widened part is ball-shaped or not.

Figure 3B:
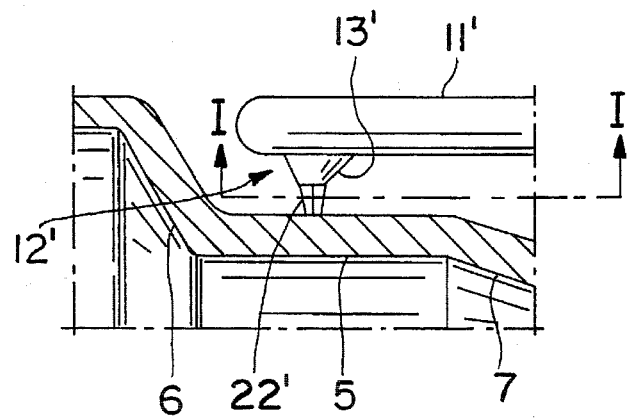
Figure 3C:
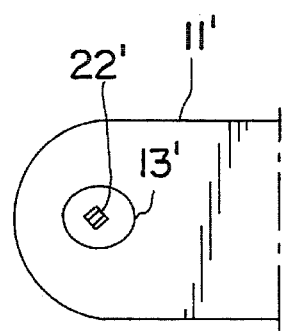

The end of the actuating rod 10 is provided with a cross-bar 15 from which two supporting rods 11',11" extend backwards towards the container 1. The centerlines of the two supporting rods 11',11" and of the actuating rod 10 are located in a common plane. The supporting rods are each attached to the cylindrical part 5 of the tubular part 2 by means of a frangible connection 12' respectively 12". The size of the frangible connections is chosen such that the outside of the supporting rods is in alignment with the outer side of the cylinder 1. Referring to FIGS. 3*b* and 3*c*, the frangible connection 12' comprises a part 13' substantially shaped as a truncated cone integrally formed with the respective supporting rod in such a way that the base of the truncated cone is joined to the supporting rod. The tip of the truncated cone is joined to the cylindrical part 5 by means of a narrow bridge 22', preferably in the form of a truncated pyramid. The part 13' of course also may have a half-spherical shape or any other suitable tapering shape.

Frangible connection 12", which is not shown in FIGS. 3*b* and 3*c*, is identical to frangible connection 12' and has parts identical to those described immediately above.

It is preferable that the width of the supporting rods (11',11") is greater than the outer diameter of the tube 4 in at least one point in the vicinity of the tube 4.

The cross bar 15 is provided with a tab 14 for actuating the actuating rod. The outer end of the actuating rod 10 may be provided with a protective, preferably circular disc 16, which is perpendicularly oriented relative to the actuating rod. This optional protective disc 16 is indicated with dashed lines in FIG. 2.

The supporting rods 11',11" in a preferred embodiment are provided with kerbs or cut-out parts 19',19", located between the cross bar 15 and a plane touching the periphery of the tip of the tube 4 at the outermost part of the edge 9. These kerbs will function as hinges when the frangible seal is broken by bending the tab 14 sideways around an axis parallel to the cross bar 15. This will result in that the membrane 3 is ruptured in a particularly controlled way. The membrane starts to rupture at the part of the membrane which is located furthest away in the direction which is opposite to the direction the tab is bent and the rupture will continously progress around both sides of the rod 10. In the final stage the rod 10 will roll upon the rounded edge 9 of the opening 8 resulting in that the edge of the rod 10 still being joined to the membrane 3 will move more or less perpendicularly to the inside wall of the opening 8, thus minimizing the risk that any part of the membrane is drawn outwards through the opening 8 before rupturing.

The devices are normally delivered in a sterile condition in so called "blister packages", which to some extent protect the device during transport and storage. However, the device has to be handled and manipulated by the user before use when the device is taken out of the package and during the interval up to the actual use of the device. During this the risk is great that the tip of the actuating rod is subjected to a force which easily may lead to a rupturing of the seal even if the force is small since the arm of leverage of the actuating rod has to be comparatively large and the seal has to be comparatively thin in order that the seal may rupture in the desired, clearly defined way. The supporting rods will however counteract any such force and thus guard against an unintentional rupturing of the seal during this handling or manipulation of the device.

The fact that the outer side of the supporting rods are aligned with the outer side of the cylinder means that the frangible connections between said rods and said cylinder to some extent is protected against an accidental breaking since this design minimizes the the risk that the connections are subjected to undesirable forces sufficient to break them. Such forces might for instance arise if the parts of the rods being located in the vicinity of the connections are caught in the blister package during extraction.

The device according to the invention can be opened in several different ways, all ensuring a correct opening of the frangible seal. Thus the device can be opened by lightly striking the tip of the actuating rod, i.e. actually the cross-bar, in the longitudinal direction of the device and more or less perpendicularly against a surface. Even if the direction of the movement deviates from the perpendicular, the fact that the tip is stabilized laterally by the supporting rods will give the actuating rod a movement which is mainly longitudinal, having the result that forces having about the same magnitude will be transmitted simultaneously from the periphery of the actuating rod to the joint between seal and rod. This means that the seal will break in a clear, well-defined way around the entire periphery.

Other ways of opening the device are for instance twisting the actuating rod around its longitudinal axis or tipping the actuating rod to the side by means of the tab attached to the cross-bar. In both cases the supporting rods will act in a similar way as described above.

Although it in principle is possible to accidentally touch the tube and the part of the conical part adjacent thereto, the supporting rods also will define an area which is to be kept sterile, since the rods in conjunction with the cross-bar give a clear visual indication of the area which must be kept sterile. It would of course be more difficult to touch the tip of the tube accidentally if the cross-bar is provided with the protective disc referred to above.

The provision of at least one part on the supporting rods and/or on the actuating rod having a width being greater than the diameter of the tube or the provision of the protective disc safeguards the sterility of the tube 4 and of the adjacent part of the conical part 7 even if the device unintentionally is put down on a table or similar prior to use.

The device is made of a thermoplastic material, as mentioned above. Preferred materials are polyolefins and particularly a homopolymer of polypropylene.

Some of the above-mentioned features also are important when the device is manufactured by means of the mould apparatus according to the invention as set forth in the attached claims and as illustrated in a preferred embodiment in FIGS. 4–11. These drawings also illustrate a method for manufacturing the device, preferably, but not exclusively, used in conjunction with the above mould apparatus.

Figure 10:
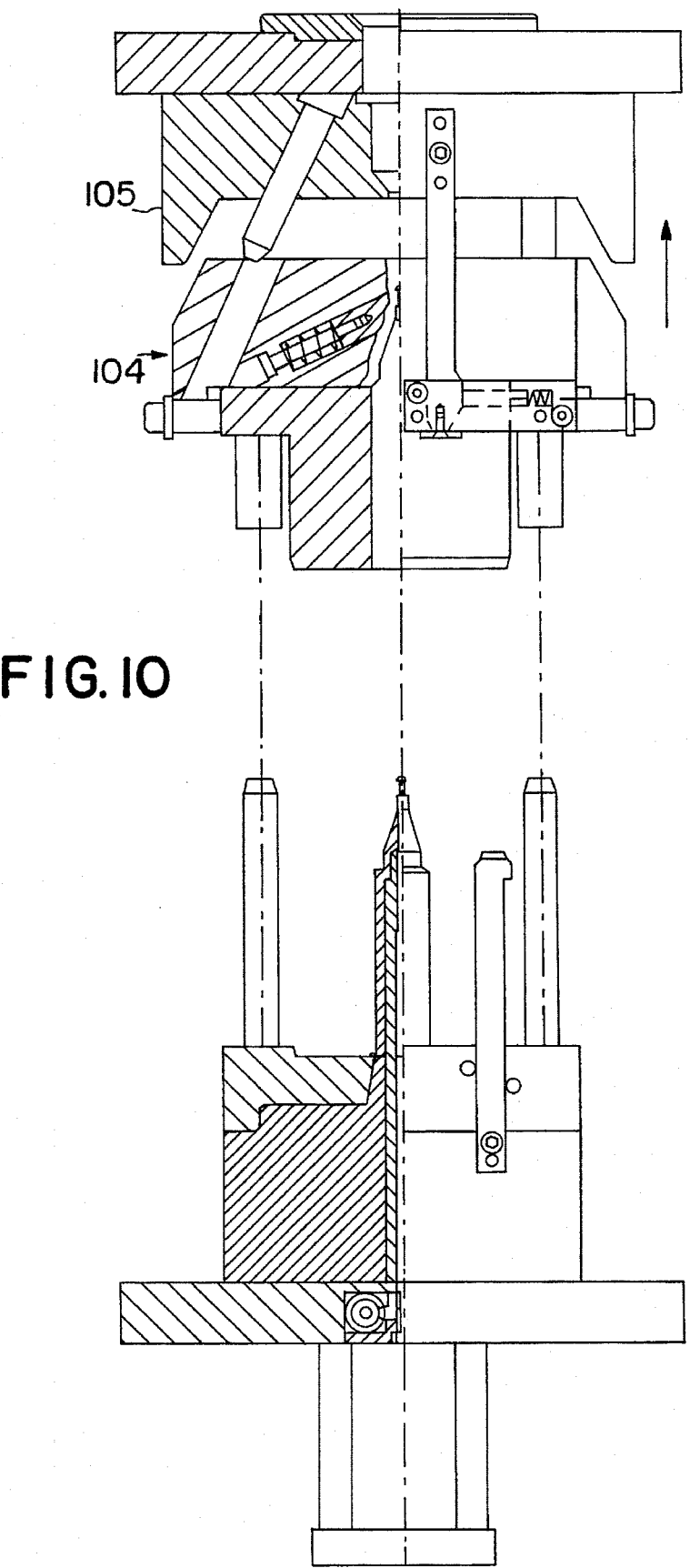
Figure 11:
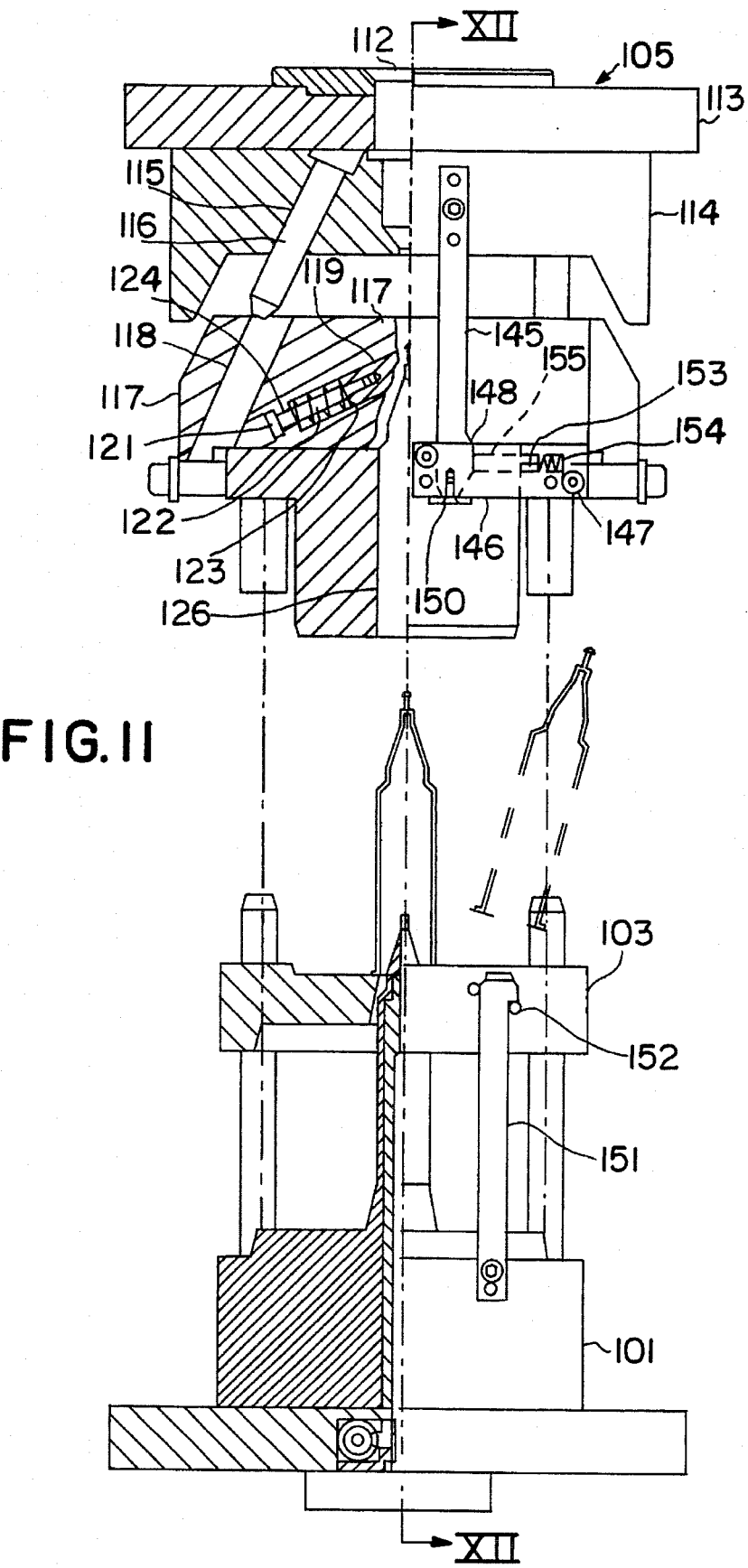

As can be seen in the drawings, especially in FIGS. 10 and 11, the mould apparatus for manufacturing the device comprises four main parts, namely a first block 101 carrying a core 102 for shaping the interior of the device, an ejector part 103, a second block 104 containing a mould for shaping the exterior of the device including the actuating rod and the supporting rods, and a third block 105 through which the molten plastics material is injected into the mould. The main parts are arranged consecutively in this order along a center line indicated with the dash-dotted line 106 coinciding with the longitudinal center line of the device and are movable relative to each other along this line. A horizontal section through the mould apparatus would be mainly square in configuration and the main parts are guided in their movement relative to each other by means of four guiding rods extending in parallel to the center line 106 through bores arranged at the corners of the square configuration. Only two of these guiding rods are illustrated in the drawings, one rod 107 being fixedly attached to said first block 101 and extending through bores 108 and 109 in said ejector part 103 respectively in said second block 104, each being provided with a respective bushing 108' and 109'. A second rod 110 is attached to the third block 105 and extends through a bore 111 in said second block 104 containing a bushing 111'.

Figure 4:
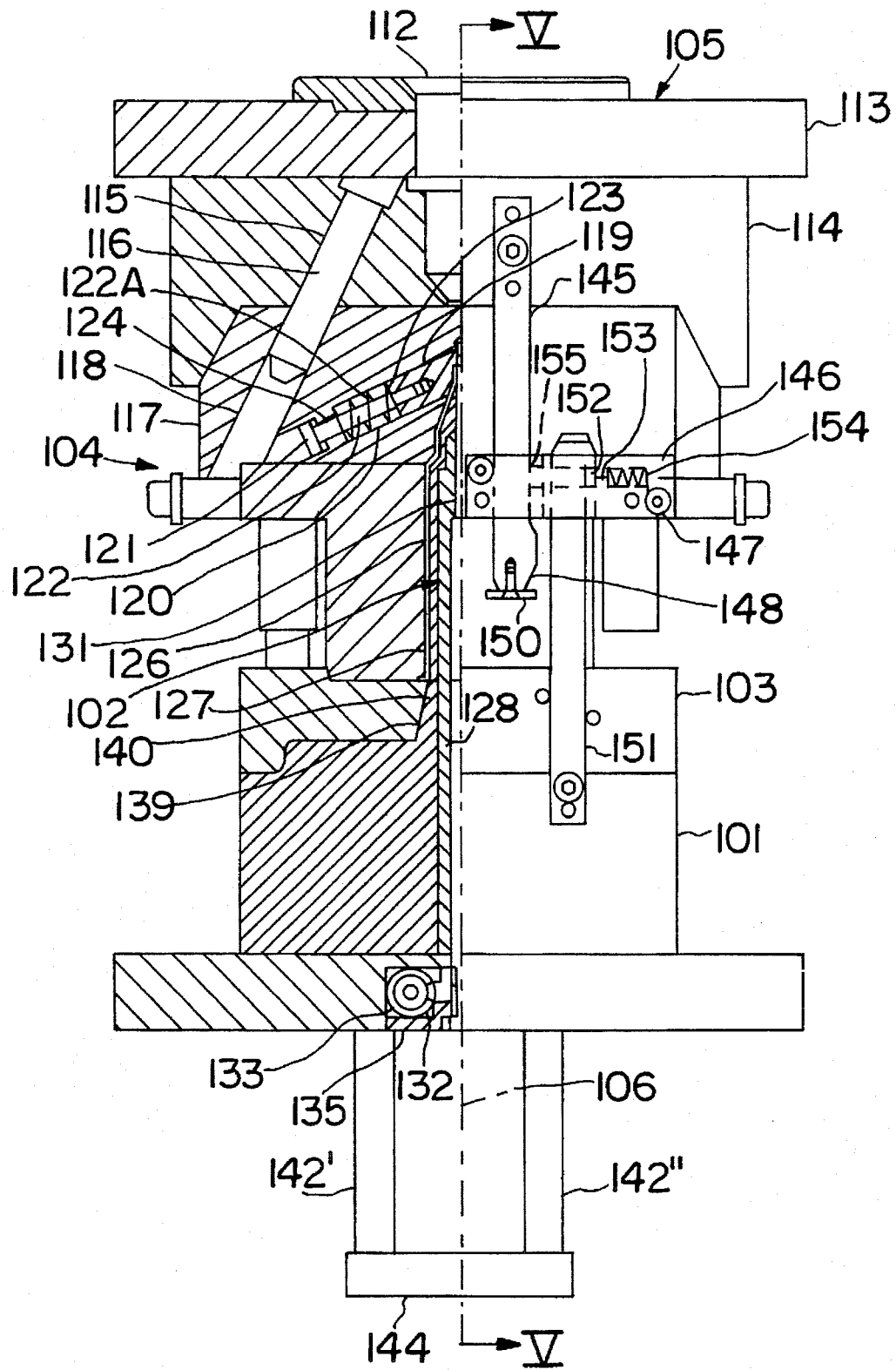

The third block 105 comprises an upper part 113 and a lower part 114, an injection nozzle 112 being coaxial with the center line 106 extending through both these parts and opening into the mould when the mould apparatus is in its closed state. As indicated in FIG. 4, two guiding rods 116 are obliquely oriented relative to the center line 106, each one extending downwardly-outwardly on opposite sides of the centerline 106 through a respective bore 115 in said lower part 114 and are fixedly attached to said lower part. The guiding rods 116 project from the underside of the lower part 114. Only one of these two guiding rods 116 is however illustrated in the drawings.

The guiding rods 116 cooperate with aligned bores 118 in first opposing mould parts 117 which are slideable inwardly and outwardly in opposite directions on a horizontal surface being perpendicular to said center line 106. These mould parts 117 are supported in the second block 104 and are provided with the mould surfaces shaping the outer side of tubular part 2 of the device including the actuating rod 10, the supporting rods 11 and the tab 14, except for the rounded edges on the end of the tube and the area in the immediate vicinity thereof.

The mould parts 117 each also contain a second mould part 119 which are slideably arranged in a respective bore or opening 120 (also shown as 120' and 120") defined in said mould part 117. The bore 120 is inclined upwardly towards the center line 106. The mould part 119 further is biased towards the center line 106 by means of a helical spring 122A surrounding a shaft portion 122 of said mould part 119 which is located in said bore, on one hand resting against a shoulder 123 on said part 119 and on the other hand resting on a flange 124 provided in said bore 120. The shaft 122 extends past said flange 124 and is provided with a stop 121 located on the opposite side of the flange. In the closed state of the mould apparatus there is a slight play between the stop and the flange.

The mould part 119 further is provided with a half-circular, horizontal, vertically oriented lip 125 (also shown as 125' and 125") defining a half-circular groove which is open downwardly. The groove is half-circular in cross-section and forms the mould surface shaping the edge 9 of the device. The lips 125',125" also define a vertically oriented, cylindrical hole located centrally in relation to the half-circular grooves. The lip 125' further has a planar, horizontal mould surface which shapes the outer surface of the frangible seal. The central hole is chamfered at the lips 125',125" in order to define an obliquely oriented surface for shaping the widened part of the actuating rod.

The second block also contains a third moulding surface in the form of a cylindrical bore 126 which is coaxial with the center line 106 and which merges into the other moulding surfaces in the second block in the closed state of the mould apparatus.

Figure 7:
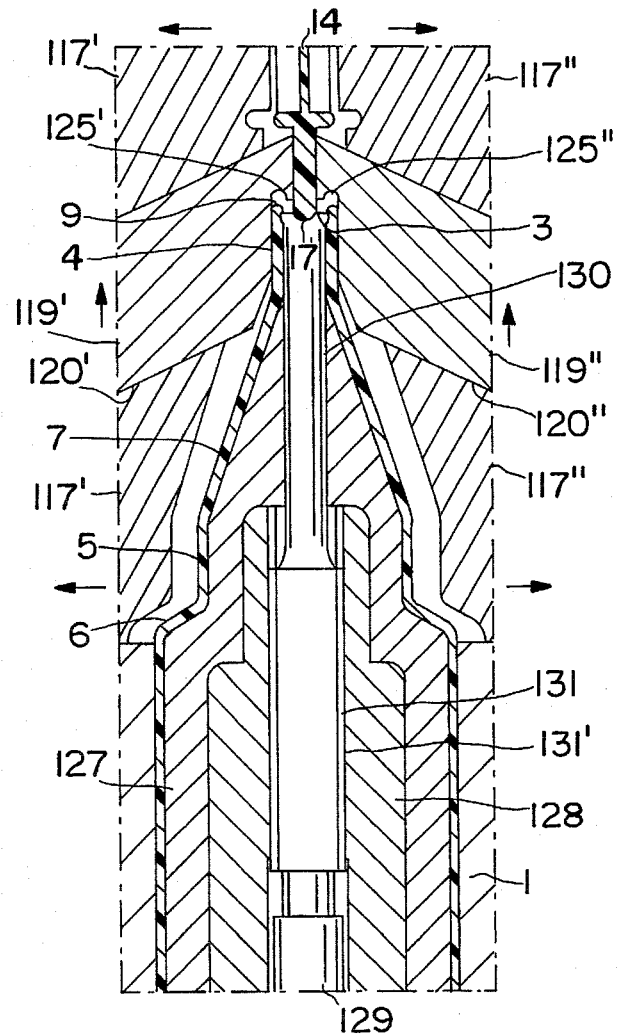

The first block 101 supports the core 102 which comprises three main components, namely an outer cylindrical sleeve 127 forming the main moulding surface for the inner side of the device and which preferably is integrally joined to said first block, an adjustment rod 129 located centrically in a central longitudinal bore in said outer sleeve 127, said adjustment rod extending through the tip 130 of the cylindrical sleeve 127 and forming the moulding surface for the inside of the tube 4 and the frangible seal 3, and finally an inner sleeve 128 supporting and guiding the adjustment rod 129. The adjustment rod is rotatably journalled in the inner sleeve and in the outer sleeve and the upper end of the adjustment rod 129 is provided with micrometer threads 131 being in engagement with corresponding interior micrometer threads 131' located in the inner bore of the outer sleeve 127 just above the upper end of the inner sleeve 128. The micrometer threads are best seen in FIG. 7. The inner sleeve and the adjustment rod extend all the way through the first block to the lower part thereof.

Figure 9:
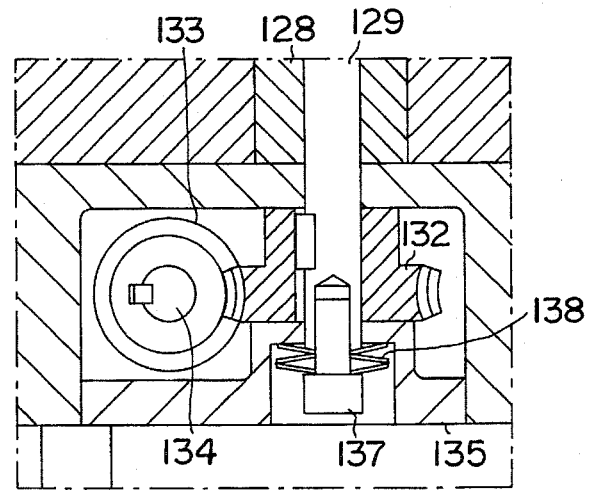
Figure 8:
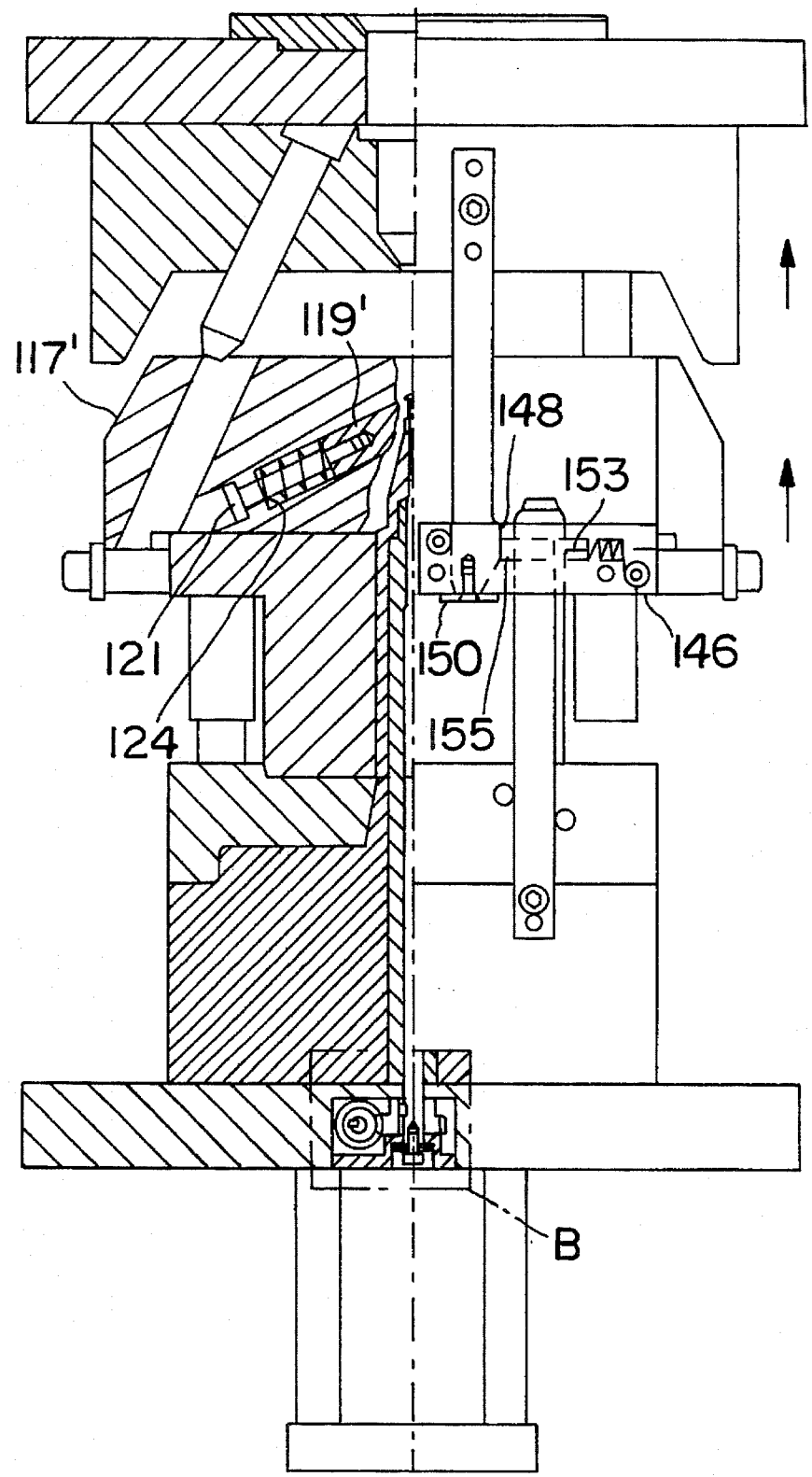

As best seen in FIG. 9, the lower end of the adjustment rod is provided with a fixedly attached, horizontally oriented gear wheel 132 which is in engagement with a horizontally oriented and rotably journalled worm gear 133 having a shaft 134 extending to the exterior of the block 101, by which means the worm gear, and consequently also the gear wheel and the adjustment rod, can be rotated. The gear wheel and the worm gear are located in a recess in the under side of the first block 101 and are covered by a plate 135 attached to the block by means of suitable screws. The adjustment rod is attached to said plate 135 by means of a screw 137 and is biased against the plate 135 by means of suitable springs, for instance Belleville washers 138 interposed between the head of the screw and the plate. In this way the position of the upper end of the adjustment rod can be exactly positioned and the thickness of the frangible seal or membrane 3 defined between the upper surface of the adjustment rod and the planar moulding surface on the lip 125' can be exactly regulated. Since the micrometer threads are located close to the upper end of the adjustment rod, the major part of any thermal expansion of the adjustment rod during the manufacturing process will be taken up by the Belleville washers and there will only be an insignificant influence on the thickness of the seal 3 (from the short length of the adjustment rod located above the threads). By this means the thickness of the seal or membrane 3 can be corrected during the manufacturing process so that all devices made will meet the same specifications in this regard. This feature is particularly important if several moulds are arranged in common, unitary main parts or blocks as is typical in the art. If the devices obtained from one of the moulds tend to deviate from the norm, this particular mould can be adjusted separately without any necessity of dismantling the entire mould system.

The ejector part 103 essentially consists of a plate or disc having a bore or hole 139 through which the core 102 projects. The part 140 of the core which extends through the hole 139 has an upwardly conically tapering shape, the hole 139 having a complementary shape. The diameter of the hole at the upper edge corresponds to the diameter of the core.

The underside of the second block rests on the ejector part 102 and is provided with two recesses 141' 141" which are connected with the main mould cavity or cylindrical bore 126. These recesses form the mould cavities for the holding tabs 18',18" in conjunction with the upper surface of the ejector part 103 when the mould apparatus is in the closed state. The ejector part 103 can be moved relative to the first block 101 by means of two ejector rods 142',142" extending through two bores (only one being shown as 143' in FIGS. 5 and 12) in parallel to the center line 106 and projecting down past the underside of the first block 101, where they are interconnected by means of an actuator block 144.

The main parts of the mould apparatus also are interconnected by means of two latch or hook means regulating the sequence of the movements of the main parts when the mould apparatus is opened.

An elongated first hook means 145 is rigidly attached to the exterior of the third block 105 and extends downwards past the second block 104 in parallel to the centerline 106 in the closed state of the apparatus.

The hook means is guided and held against the exterior of the second block 104 by means of an elongated, horizontally oriented plate 146 attached to the second block by means of suitable screws 147 provided with suitable spacers. The first hook means is provided with a cam surface 148 in the vicinity of its lower end. The lower end is also provided with a stop means 150 for engagement with the plate 146 and a surface on said second block facing downwards.

A second hook means 151 is rigidly attached to the first block 101 and extends past the ejector means 103 to the second block 104. The second hook means 151 also is held and guided against the exterior of the second block 104 by means of said plate 146. The second hook means further is provided with a horizontal shoulder 152 which may be engaged by a horizontally movable latch 153 which is biased towards its latching position by means of a spring 154. The latch 153 further is provided with an actuator 155 which may be actuated by the cam surface 148, thus moving the latch 153 out of engagement with said shoulder 152 against the action of said spring 154 and freeing the second hook means 151.

Figure 5:
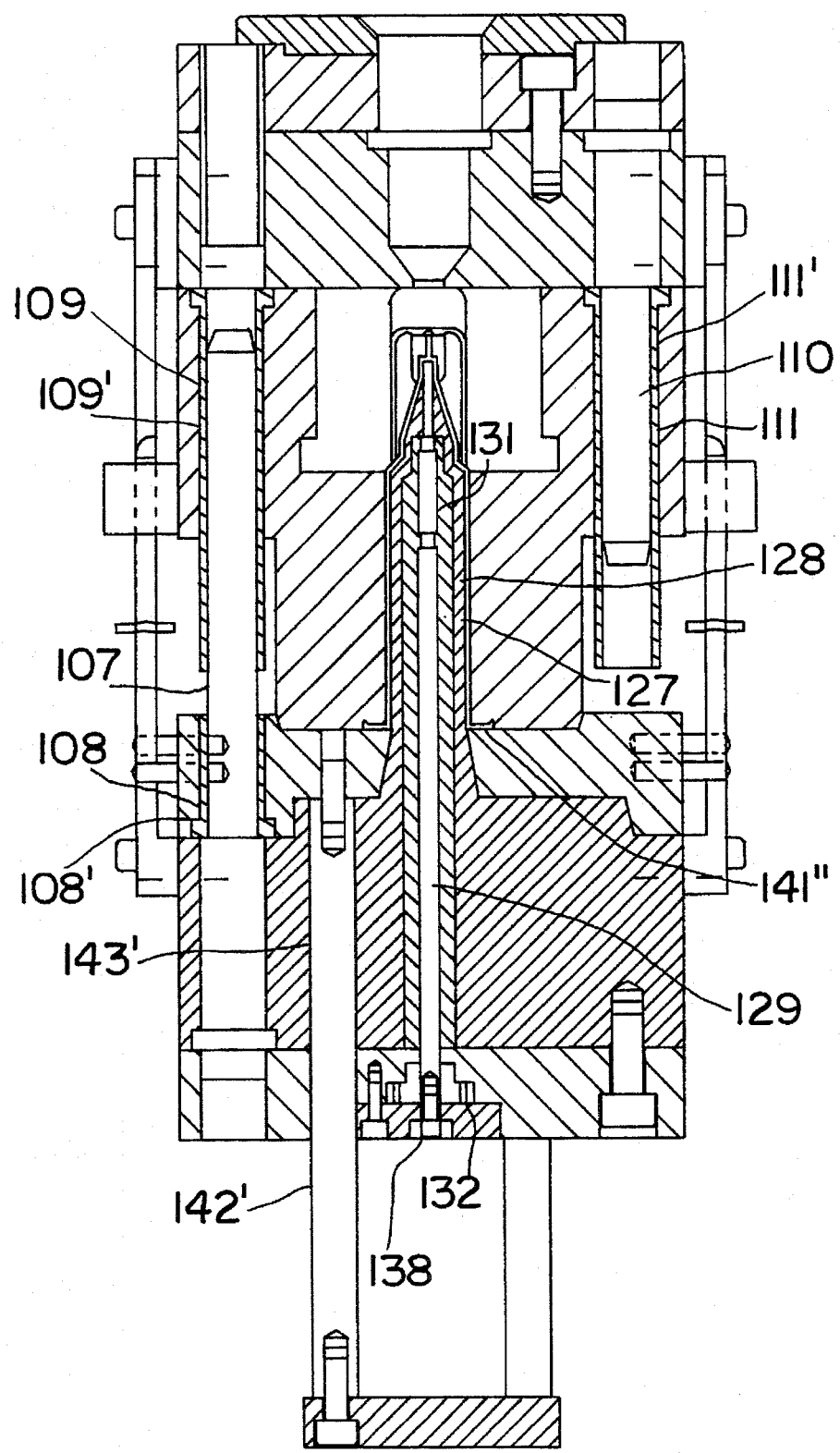
Figure 12:
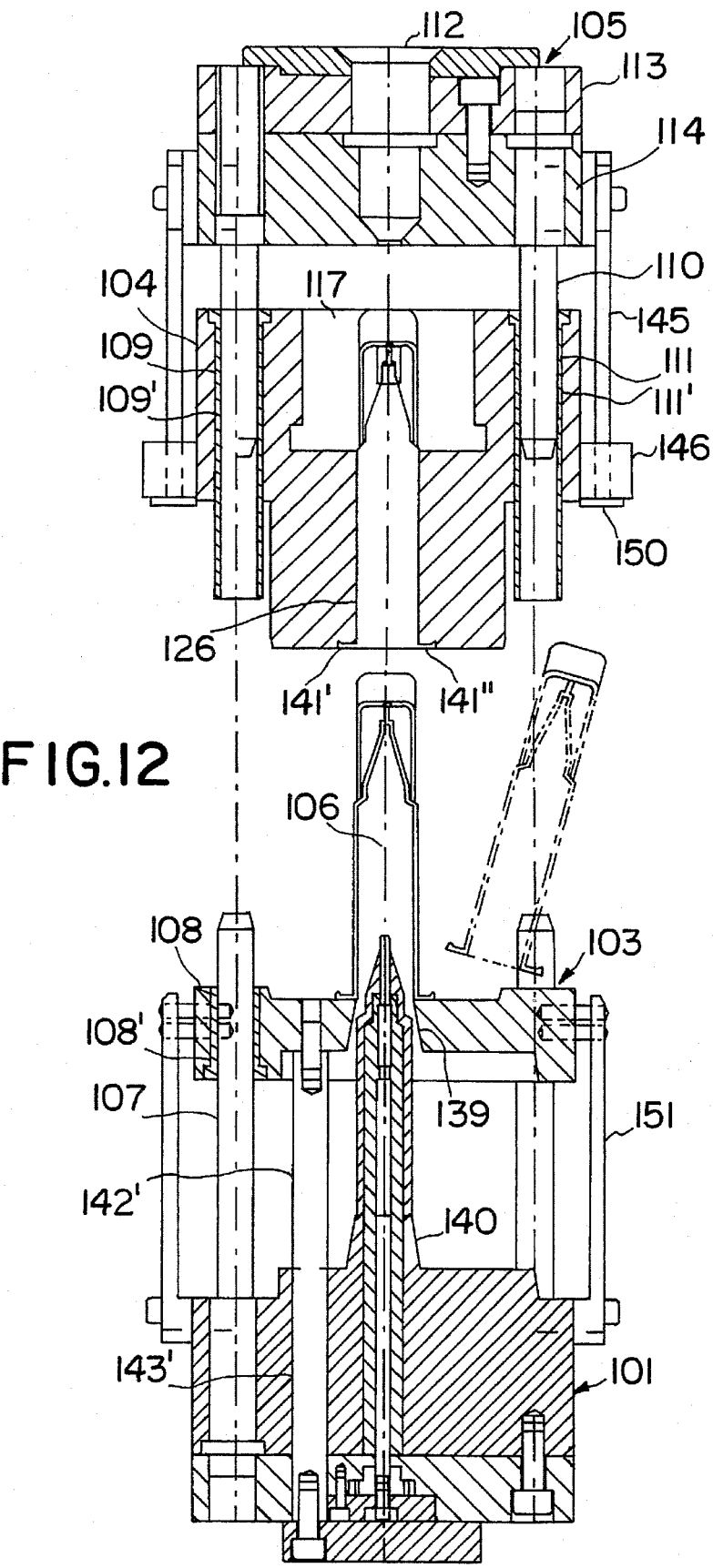

Although only one pair of hook means is described, two pairs of hook means are provided in this embodiment as is evident from FIGS. 5 and 12.

The moulding apparatus also contains cooling conduits or channels in the blocks 101 and 104 as well as in the core 102 for keeping the mould at a temperature which is sufficiently far below the solidifying temperature of the thermoplastic material to allow the molded device to harden rapidly but sufficiently high to allow the molten material to completely fill all cavities in the mould without any detrimental effect on the finished product.

THE FUNCTION OF THE MOULDING APPARATUS

FIGS. 4 and 5 show the moulding apparatus in the closed state immediately after the injection of the molten thermoplastic material and as described in detail above.

Figure 6:
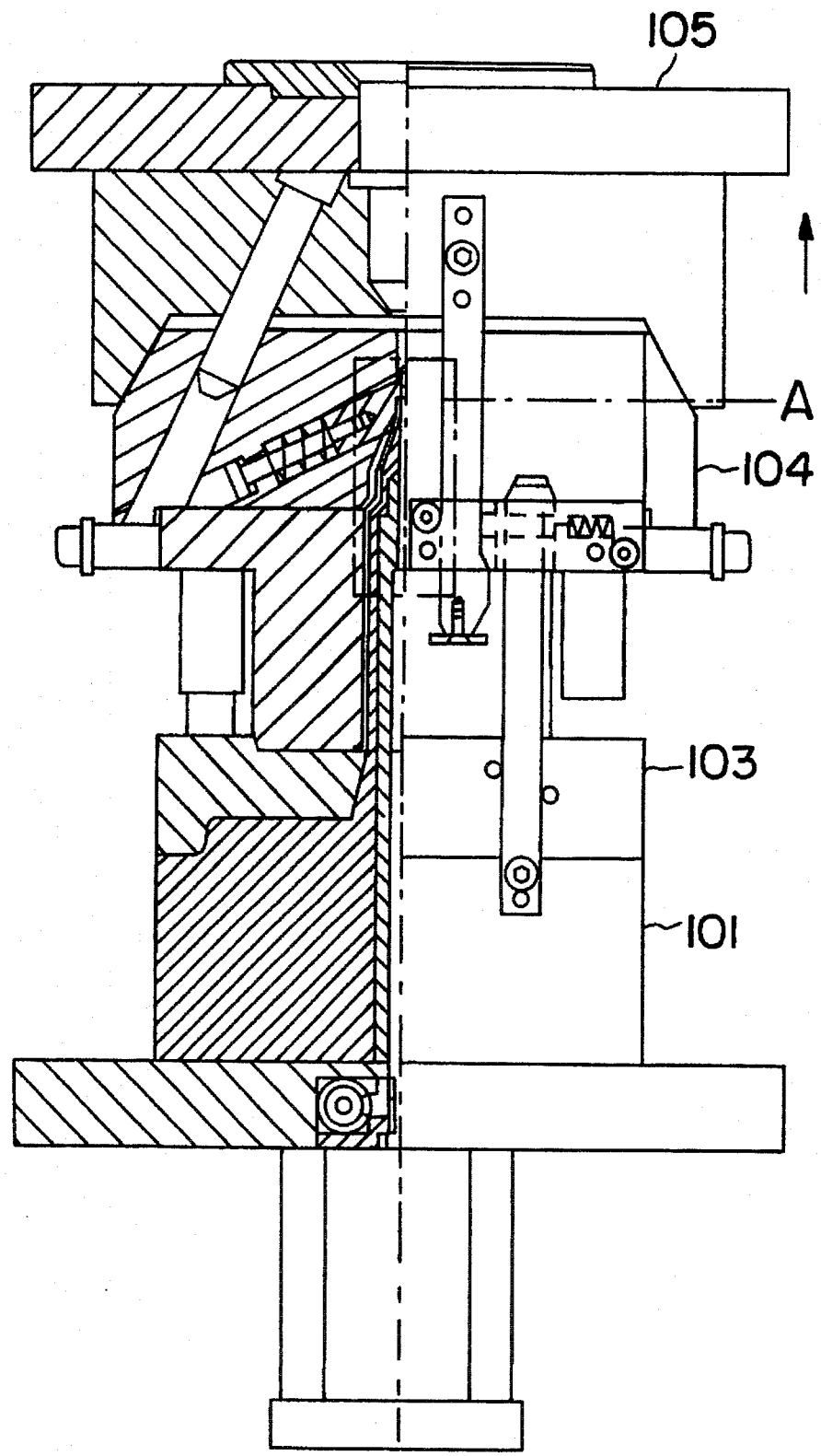

FIGS. 6 and 7 show the first step of opening the moulding apparatus after the solidification of the device. In this step the third block 105 containing the injection nozzle is moved slightly upwards relative to the other blocks. The mould parts 117',117" in the second block consequently move slightly outwards under the influence of the obliquely oriented guiding rods 116 in the obliquely oriented bores 118. The second mould parts 119',119" will however not move outwards together with the mould parts 117',117" since they are pushed inwardly under the influence of the springs 122A',122A". The outward movement of the mould parts 117',117" instead forces the second mould parts 119',119" to move vertically upwards, resulting in that the lips 125',125" move vertically upwards until they clear the edge 9 of the device. The fact that the lips 125',125" are provided with the obliquely oriented surfaces will facilitate the release of the device from the mould and minimize the risk for damage to the seal and the edge at the end of the tube.

The free play between said stop 121 and said flange 124 is dimensioned in such a way that the stop 121 engages the flange 124 at the moment when the lips 125',125" clear the edge 9. This results in that the mould parts 119',119" move horizontally outwards together with the mould parts 117', 117" in the second step of opening the mould apparatus shown in FIG. 8, thus also releasing the outer side of the tube 4 and the adjacent part of the conically tapering part 7.

This movement, and thus also the second step of opening the mould, ends when the stop means 150 engages the respective plates 146 and said under side of the second block 104. Prior to this, the cam surface 148 has engaged the actuator 155, releasing the second hook means 151. In the third step of opening the mould apparatus shown in FIG. 10, the second and third blocks 104 and 105 thus move together away from the first block 101 and the ejector means 103. In this third step the outside of the cylinder 1 is released and freed from the mould apparatus.

In the final step illustrated in FIGS. 11 and 12 the ejector means 103 is moved upwardly relative to the first block 101 by means of the ejector rods 142',142". In this way the finished device is pushed off the core 102 and entirely released from the mould apparatus, whereafter the device can be transmitted to a filling station.

Apart from the widened part of the actuator rod there are two further features of the device that are important when the device is made in the mould apparatus described above. Both mainly relate to the fact that the core is cantilevered from the first block.

The first one of these features is the provision of two symmetrically arranged supporting rods with frangible connections. The mould apparatus works with relatively high pressures when the molten material is injected into the mould cavity. Although the main part of the molten material is introduced through the annular space defining the frangible seal, the injection pressure is also transmitted to the interior of the mould cavity via the comparatively small passage defining the frangible connection between supporting rod and container. This pressure will give cause comparatively great forces on the core and thus cause a deflection thereof since these forces act close to the free end of the cantilevered core. Such a deflection is however not desirable, since the width of the frangible seal or membrane in the device when designed for use in the urethra is about one tenth of a millimeter, and any deflection of the core of this size or greater would result in that the actuating rod is joined directly to the wall of the tube. An attempt to rupture the seal by means of the actuating rod might in this case result in that the wall of the tube breaks instead of the frangible seal, causing precisely those rough edges which can not be accepted in a device of this kind. The provision of two symmetrically arranged, opposing frangible connections will cause two opposing forces to be introduced into the mould cavity which effectively neutralize each other.

However there still might be minor deflections or deviations in the position of the core. Such deflections may be difficult to avoid, again largely due to the fact that the core is comparatively long and cantilevered. The second feature will compensate for this and consists in that the tube is provided with an inner diameter which is greater on the side of the seal facing the interior of the device than on the side facing the open end of the tube, i. e. that the diameter of the core shaping this part of the tube is larger than the outer diameter of the lip. This feature is best seen in FIG. 7. This will have the result that minor deviations in the position of the tip of the core are compensated from the viewpoint of achieving a faultless frangible seal around the entire periphery of the actuating rod.

As discussed above, an important feature in the method of manufacturing the device is that the major part of the molten material is introduced into the mould through the comparatively narrow slit in the mould defining the frangible seal. In the moulding apparatus described above, the mould cavities for shaping the actuating rod and the supporting rods will be filled first and a minor amount of molten material will bulge out through the narrow passages defining the frangible connections into the parts of the mould cavities shaping the cylinder and the tubular part. The molten material then almost entirely will flow through the space defining the frangible seal. Since the molten material thus continuously flows past the location of the frangible seal and the adjacent parts of the device, the homogeneity of the material in those parts of the finished device is ensured, the risk being eliminated that two streams having cooler front surfaces meet in those parts, forming an imperfect union, which might lead to that the device is ruptured or breaks in another place than at the frangible seal.

The molten material then flows on through the parts of the mould cavity defining the tube and the conically tapering part, on the way encapsulating the bulges of material projecting from the narrow passages defining the frangible connections. These bulges thus will be firmly united with the main body of the device and the frangible connections will be homogeneous and be given a good quality in the same way as discussed in the preceding paragraph in connection with the frangible seal.

As discussed above, the mould is cooled in order to allow the shaped device to harden within a reasonable time. If polypropylene is used the temperature of the molten material suitably is about 230–250 degrees Celsius, the temperature of the moulding apparatus being kept at 35–40 degrees Celsius. This great temperature difference of course to some extent will influence the flow characteristics of the molten material, which is undesirable in the narrow mould parts around the frangible seal, since the desired homogenity in these parts might be impaired. The method according to the invention therefore also makes a virtue of the fact that it is very difficult to cool the tip of the core and the other parts of the mould cavity in the vicinity thereof as efficiently as the other parts of the mould and these parts consequently are allowed to be heated by the stream of hot, molten material. A result is that the material will flow more easily in these parts and especially through the very narrow space defining the frangible seal, by which means the the mould cavities in this vicinity are particularly well filled and the homogenity of the material is yet more enhanced. The relatively high temperature will also re-melt so called "cold welds" should such occur in spite of all.

Since the mass of the relevant parts is small, these parts will cool rapidly to the temperature of the main part of the mould apparatus as soon as the the stream of molten, hot material is stopped.

The method according to the invention thus also eliminates the necessity of elaborate and expensive cooling arrangements in and around the tip of the core.

We claim:

1. A prefilled, disposable device for introducing a pharmacologically active substance into a body cavity of a patient, comprising:
    a container for the substance said container having opposite ends;
    a tubular part integrally formed with and extending from one end of said container, said tubular part having a first end communicating with the container and having a second end, intended to be inserted into said cavity, including a rounded forward edge forming an opening, wherein said rounded forward edge acts to alleviate any discomfort which may be experienced by the patient when the second end is inserted into said cavity;
    a frangible seal integrally formed with said tubular part and sealing said opening, said seal having an inner side facing the inside of said device and an outer side facing the outside, said seal being located a slight distance within said opening;
    an actuating rod integrally formed with and extending from the outer side of said seal and projecting through said opening to the outside of the device, said actuating rod being arranged to rupture and remove said seal upon actuation and before the insertion of said second end into said body cavity;
    at least one supporting rod formed integrally with said actuating rod and extending toward said container, said supporting rod being connected to said container by means of a frangible connection; and
    means for sealing the opposite end of said container and for forcing said active substance from said container and through said opening after said seal is ruptured;
    wherein said supporting rod serves as a safeguard against an accidental rupturing of said seal and as a guide for a controlled movement of said actuating rod, when actuated, in order to ensure a correct rupture of said frangible seal as well as to serve as a handle for actuating said actuating rod, said supporting rod in conjunction with said actuating rod also defining and protecting an area of said tubular part which is to be kept sterile.

2. A device according to claim 1, wherein said actuating rod is provided with two supporting rods arranged on opposite sides of said actuating rod in a common plane through the longitudinal center line of said actuating rod.

3. A device according to claim 2, wherein said tubular part has a conically tapering part between said first and second ends, said conically tapering part ensuring a fluid-tight fit between said tubular part and the opening of said body cavity when said second end is inserted into said body cavity.

4. A device according to claim 3, wherein said container has an annular shoulder adjoining the first end of said tubular part, and wherein said tubular part includes a cylindrical portion adjoining said annular shoulder.

5. A device according to claim 4, wherein each said supporting rod is connected to said container on said cylindrical portion.

6. A device according to claim 4, wherein said cylindrical part merges into said conically tapering part and is connected to said annular shoulder, each of said supporting rods being connected to said cylindrical part.

7. A device according to any one of claims 1–6, wherein said container has two open ends, one end thereof being closed by said tubular part, and said means for forcing the active substance out of said container through said tubular part comprises a plunger inserted into the opposite open end of said container, and wherein the contents of the container can be discharged through said opening in said tubular part when the frangible seal has been broken.

8. A device according to any one of claims 1–6 wherein, said actuating rod is provided with a disc-shaped member oriented perpendicularly to the longitudinal extent of said actuating rod in order to further protect and define said area to be kept sterile.

9. A device according to any one of claims 1–6, wherein said connection between said supporting rod and said container has a substantially half-spherical shape formed integrally with said supporting rod whose flat side is attached to said supporting rod, the actual frangible connection being formed by a short bridge formed integrally between the crown of the half-spherical shape and said container.

10. A device according to any one of claims 1–6, wherein the cross-sectional dimension of said actuating rod at a portion adjacent to the seal is only slightly less than the interior width of said tubular part at the location of said seal, said seal being in the form of a narrow peripheral band around said portion of said actuating rod.

11. A device according to claims 1–6 wherein said seal is a membrane.

12. A device according to any one of claims 3–6, further comprising a cross-bar attached to said rod end and extending perpendicularly to the longitudinal direction of said actuating rod and a tab attached to said cross-bar, wherein each of said supporting rods are provided with a cut-out located at a point on said rod between the cross bar and a plane extending from said second end in a direction perpendicular to the longitudinal direction of said actuating rod said cut-out serving as a hinge when the cross bar and tab are bent sideways in a direction perpendicular to the plane of the tab.

13. A method for manufacturing the device recited in claim 1 comprising the steps of:

providing a mold having a first mold part comprising a core having the desired shape of the interior of said container and said tubular part, and a second mold part having the general configuration of the outer side of said device including said actuating rod and said supporting rod, wherein said first and second mold parts define a mold cavity therebetween; and injecting thermoplastic material in molten form into said mold at that part of said mold which defines said supporting rod and said actuating rod, by which means said molten material is forced to pass mainly through the mold cavity in said mold defining said frangible seal before forming the container and said tubular part.

14. A mold apparatus for making a device according to claim 1 comprising a first mold part containing a core, said core defining the interior of said container and said tubular part, and a second mold part defining the outer side of said device, said first and second mold parts defining a mold cavity therebetween and being longitudinally movable with respect to each other for opening said mould cavity and for the ejection of said device, wherein said core is longitudinally movable with respect to said mould cavity by means of micrometer adjustment threads, by which means the thickness of said frangible seal defined between the tip of said core and said mould cavity at the end of said tubular part can be finely adjusted before and during the manufacturing process.

15. A mould apparatus according to claim 14, wherein the core includes an adjustment rod located in a central, longitudinal bore in the core, the core being fixed and the adjustment rod being movable by means of said micrometer threads, the tip of the adjustment rod forming the surface moulding the inner side of said frangible seal, said micrometer threads being located on the outside of said adjustment rod and on the inside of said bore in the core, by which means the position of the tip of the adjustment rod can be finely adjusted by rotating the rod.

16. A mould apparatus according to claim 15, wherein said micrometer threads are located close to tip of the adjustment rod.

* * * * *